United States Patent
Yamamoto (10) Patent No.: US 8,276,638 B2
(45) Date of Patent: Oct. 2, 2012

(54) INTERMITTENT CUTTING TRANSFERRING DEVICE

(75) Inventor: Hiroki Yamamoto, Kanonji (JP)

(73) Assignee: Unicharm Corporation, Ehime (JP)

( * ) Notice: Subject to any disclaimer, the term of this patent is extended or adjusted under 35 U.S.C. 154(b) by 203 days.

(21) Appl. No.: 12/390,099

(22) Filed: Feb. 20, 2009

(65) Prior Publication Data

US 2009/0321021 A1  Dec. 31, 2009

(30) Foreign Application Priority Data

Jun. 30, 2008  (JP) ............... P2008-171894

(51) Int. Cl.
*B26D 7/18* (2006.01)
*B26D 7/32* (2006.01)
*B32B 38/04* (2006.01)

(52) U.S. Cl. .......... 156/519; 271/196; 271/276; 83/100; 83/349

(58) Field of Classification Search .......... 156/518–520; 271/196, 276; 83/100, 349

See application file for complete search history.

(56) References Cited

U.S. PATENT DOCUMENTS

| 4,016,032 A * | 4/1977 | Kankaanpaa .......... 162/305 |
| 5,137,758 A * | 8/1992 | Kistner et al. .......... 427/350 |
| 5,405,487 A * | 4/1995 | Galchefski et al. .......... 156/566 |
| 2002/0129687 A1 | 9/2002 | Eckstein et al. |
| 2004/0089516 A1 | 5/2004 | Christian et al. |
| 2006/0266465 A1 | 11/2006 | Meyer |
| 2006/0266466 A1 | 11/2006 | Meyer |
| 2007/0084580 A1 * | 4/2007 | Kahl et al. .......... 162/368 |
| 2009/0321021 A1 | 12/2009 | Yamamoto |

FOREIGN PATENT DOCUMENTS

| EP | 0113976 | 7/1984 |
| JP | 10-218471 A | 8/1998 |
| WO | 9841401 | 9/1998 |

OTHER PUBLICATIONS

European Search Report for Application No. 09773459.4 mailed Sep. 23, 2011.

* cited by examiner

*Primary Examiner* — Katarzyna Wyrozebski Lee
*Assistant Examiner* — Scott W Dodds
(74) *Attorney, Agent, or Firm* — Lowe, Hauptman, Ham & Berner, LLP (57) ABSTRACT

An intermittent cutting transferring device configured to cut a first web into individual sheets and to intermittently transfer the individual cut sheets onto a second web being continuously fed includes an upper blade roll with a blade and a lower blade roll with an anvil element. The cut sheet is configured to be sucked onto an outer peripheral surface of the lower blade roll at a position where both side edge regions of the cut sheet and a front end region thereof face an edge area of the second region while a remaining region of the cut sheet faces a center area of the second region. A suction holding force in the edge area is stronger than a suction holding force in the center area.

11 Claims, 7 Drawing Sheets

INTERMITTENT CUTTING TRANSFERRING DEVICE

RELATED APPLICATIONS

The present application is based on, and claims priority from, Japanese Application Number 2008-171894, filed Jun. 30, 2008, the disclosure of which is hereby incorporated by reference herein in its entirety.

BACKGROUND OF THE INVENTION

1. Field of the Invention

The present invention relates to an intermittent cutting transferring device configured to cut a continuum of film sheet into film sheets and intermittently transfer the film sheets to a web being continuously fed.

2. Description of the Prior Art

An intermittent cutting device is used in processes of manufacturing disposable diaper. Conventionally, the intermittent cutting device is configured to cut a continuum of film sheet, printed with patterns such as characters and figures, into the film sheets, and intermittently transfer the film sheets to a web being continuously fed.

Generally, the film sheet is configured to have lower breathability, thinner thickness and more flexibility than the web. That is, the film sheets have characteristics of low rigidity and resilience.

Such an intermittent cutting transferring device includes: an upper blade roll including blades on an outer peripheral surface; and a lower blade roll including, a stationary blade on an outer peripheral surface and a mesh suction plate over the entire outer peripheral surface (for example, see Japanese Patent Application Publication No. Hei 10-218471 (pp 4 to 6 and FIG. 3)).

The upper blade roll and the lower blade roll are configured to rotate at approximately the same peripheral velocity in directions opposite from each other. In addition, these rolls are also configured to rotate at peripheral velocities higher than the velocity in which the continuous film sheet is fed to the lower blade roll, and to rotate at peripheral velocities approximately equal to or lower than the feeding velocity of the web.

Hereinafter, steps of intermittently transferring the film sheet to the web will be described using the intermittent cutting transferring device described above.

In a first step, the intermittent cutting transferring device guides the continuum of film sheet between the blade and the stationary blade with the continuum of film sheet being sucked onto the outer peripheral surface of the lower blade roll by the suction through the mesh suction plate formed over the entire outer peripheral surface of the lower blade roll.

At this time, the continuum of film sheet slides on the outer peripheral surface of the lower blade roll to be guided between the blade and the stationary blade since the upper blade roll and the lower blade roll rotate at the peripheral velocities higher than the velocity in which the continuous film sheet is fed to the lower blade roll.

In a second step, the intermittent cutting transferring device intermittently cuts the continuum of film sheet by bringing the blade and the stationary blade into contact with each other, and thus forms a film sheet.

In a third step, the intermittent cutting transferring device guides the film sheet which is cut to the web while the film sheet which is cut is being sucked onto the outer peripheral surface of the lower blade roll by the suction through the mesh suction plate formed over the entire outer peripheral surface of the lower blade roll.

In a fourth step, the intermittent cutting transferring device transfers, to the web, the film sheet which is cut and sucked onto the outer side surface of the lower blade roll.

However, the conventional intermittent cutting transferring device described above has the following problem. That is, with the conventional intermittent cutting transferring device, a wrinkle is formed in the film sheet which is cut due to conditions such as unevenness in weight (weight per unit area) of the film sheet, contact failure of the blade and the stationary blade, and occurrence of wear in the blade.

Accordingly, the film sheet which is cut is transferred to the web with the wrinkle being formed in the film sheet. Particularly, since the film sheet which is cut has the characteristics of low rigidity and resilience, once the wrinkle is formed, the film sheet cannot be restored to its original state.

SUMMARY OF THE INVENTION

Thus, the present invention has been made in view of such a situation, and has an object of providing an intermittent cutting transferring device which can suppress the formation of a wrinkle in a film sheet and which can smooth out a wrinkle formed in the film sheet even when the wrinkle is formed in the film sheet.

To solve the above situation, the present invention comprises the following aspects. A first aspect is summarized as an intermittent cutting transferring device configured to cut a continuum of film sheet into film sheets and to intermittently transfer one of the film sheets which are cut, herein after referred to as "a cut film sheet", to a web being continuously fed. The intermittent cutting transferring device comprises an upper blade roll provided with at least one blade on its outer peripheral surface and a lower blade roll provided with at least one stationary blade on its outer peripheral surface and having a plurality of suction holes formed on the outer peripheral surface. The upper blade roll and the lower blade roll rotate at approximately the same peripheral velocity in directions opposite from each other, rotate at the peripheral velocities higher than a velocity in which the continuum of film sheet is fed to the lower blade roll, and rotate at the peripheral velocities approximately equal to or lower than a feeding velocity of the web. The continuum of film sheet is guided between the blade and the stationary blade with the continuum of film sheet being sucked onto the outer peripheral surface of the lower blade roll by a suction through the suction holes formed in a first region on the outer peripheral surface of the lower blade roll. The continuum of film sheet is intermittently cut by bringing the blade and the stationary blade into contact with each other, and forms the cut film sheet. The cut film sheet is guided and transferred to the web while the cut film sheet is being sucked onto the outer peripheral surface of the lower blade roll by a suction through the suction holes formed in a second region on the outer peripheral surface of the lower blade roll. The cut film sheet is sucked onto the outer peripheral surface of the lower blade roll at a position where both side edge regions of the cut film sheet and a front end region thereof in a proceeding direction face an edge area of the second region while a remaining region of the cut film sheet faces a center area in the second region. And a suction holding force in the edge area is stronger than a suction holding force in the center area.

According to the present invention, the intermittent cutting transferring device can be provided which can suppress the formation of a wrinkle in the film sheet and smooth out a wrinkle formed in the film sheet even when the wrinkle is formed in the film sheet.

DETAILED DESCRIPTION OF THE PREFERRED EMBODIMENTS

Hereinafter, one example of an intermittent cutting transferring device according to the present invention will be described with reference to the drawings. Note that, throughout the drawings, the same or similar portions are denoted by the same or similar reference numerals. However, the drawings are schematic, and it should be noted that the dimensional proportions and others are different from their actual values.

Thus, specific dimensions and the like should be determined based on the descriptions given below. It is needless to say that the dimensional relationships and dimensional proportions may differ from one drawing to another in some parts.

[First Embodiment]
(Configuration of Intermittent Cutting Transferring Device)

Figure 1:
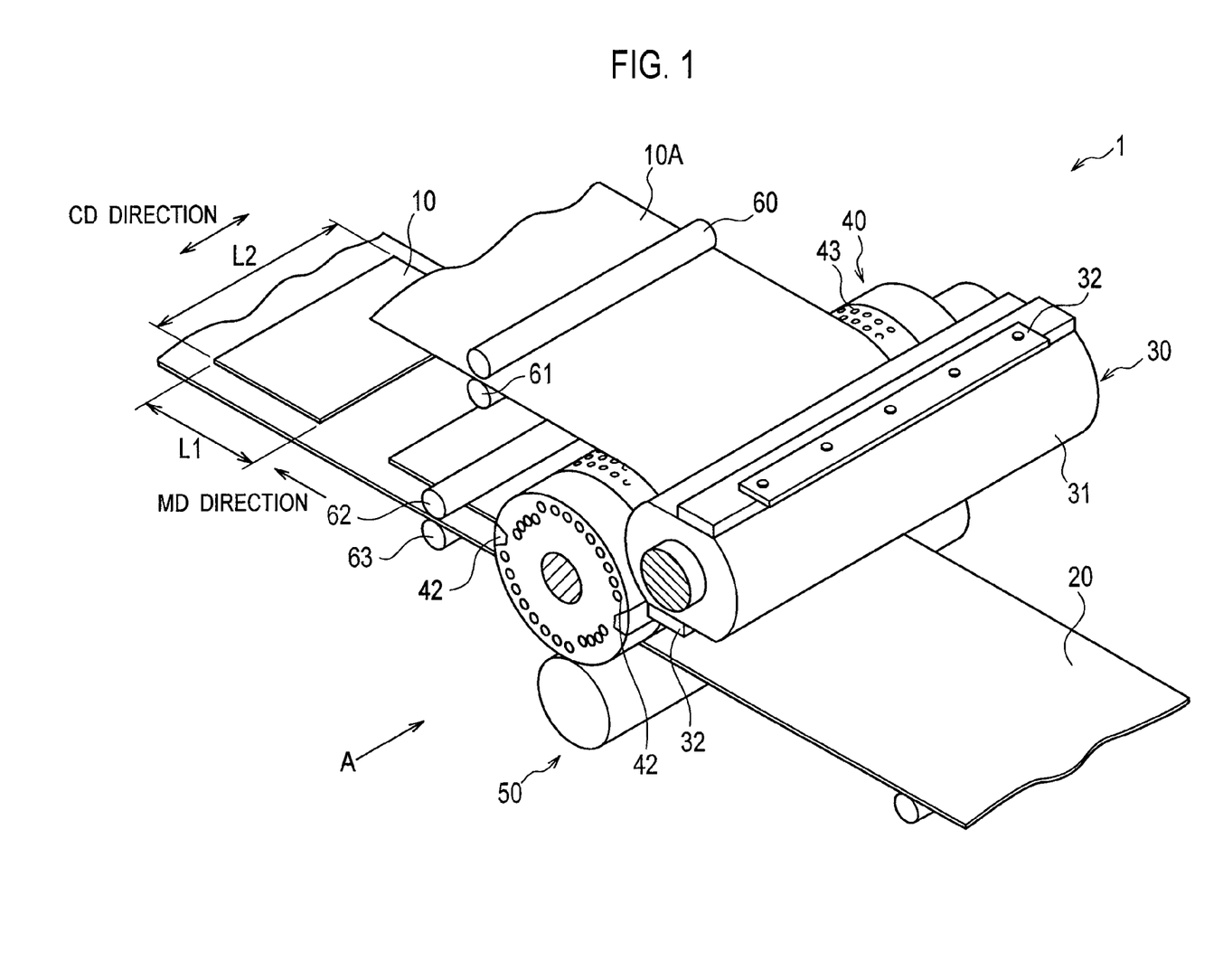
FIG. 1 is a perspective view showing an intermittent cutting transferring device 1 according to a first embodiment.
Figure 2:
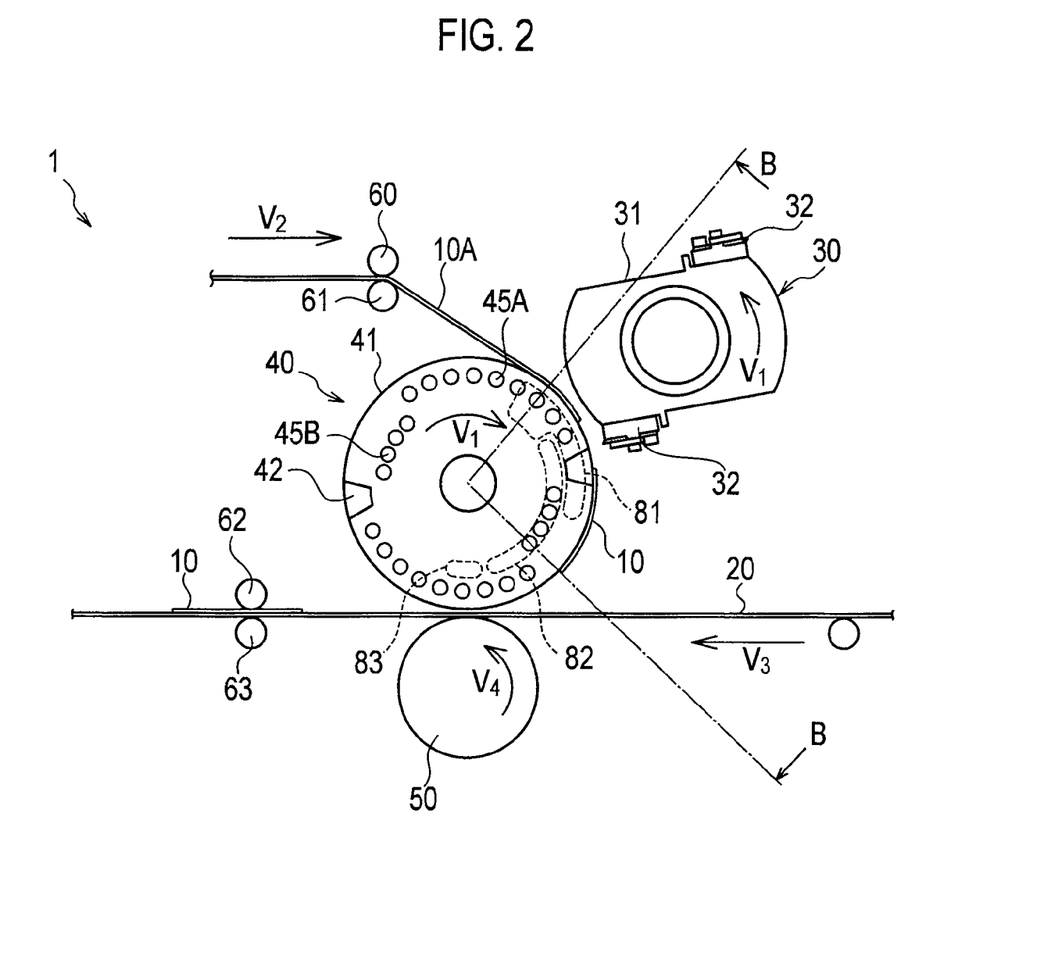
FIG. 2 is a side view (view on arrow A of FIG. 1) showing the intermittent cutting transferring device 1 according to the first embodiment.

First, the configuration of the intermittent cutting transferring device according to a first embodiment will be described with reference to the drawings. FIG. 1 is a perspective view showing an intermittent cutting transferring device 1 according to the first embodiment. FIG. 2 is a side view (view on arrow A of FIG. 1) showing the intermittent cutting transferring device 1 according to the first embodiment.

As shown in FIGS. 1 and 2, the intermittent cutting transferring device 1 is configured to intermittently transfer a cut film sheet 10, obtained by cutting a continuum of cut film sheet 10A printed with patterns such as characters and figures, to a web 20 being fed continuously.

Note that a length (L1) of the cut film sheet 10 in its feeding direction (hereinafter called the "MD direction") is shorter than a length (L2) thereof in a direction crossing the MD direction (this direction is hereinafter called the "CD direction").

The intermittent cutting transferring device 1 is configured briefly of an upper blade roll 30, a lower blade roll 40, and a transfer roll 50.

Two blades 32 are provided on an outer peripheral surface 31 of the upper blade roll 30. The upper blade roll 30 rotates at a peripheral velocity ($V_1$) approximately equal to a peripheral velocity of the lower blade roll 40. The upper blade roll 30 rotates at the peripheral velocity ($V_1$) higher than a velocity ($V_2$) in which the continuum of film sheet 10A is fed to the lower blade roll 40 by a pair of driving rolls 60 and 61. The upper blade roll 30 rotates at the peripheral velocity ($V_1$) approximately equal to a feeding velocity ($V_3$) of the web 20 continuously fed by driving rolls 62 and 63, or rotates at the peripheral velocity ($V_1$) lower than the feeding velocity ($V_3$) of the web 20.

In an outer peripheral surface 41 of the lower blade roll 40, two anvil elements 42 are provided, and suction holes 43 which suck the continuum of film sheet 10A and the cut film sheet 10 are formed. The lower blade roll 40 rotates at the peripheral velocity (V1) approximately equal to the peripheral velocity of the upper blade roll 30, in a direction opposite to the direction in which the upper blade roll 30 rotates. The configuration of the lower blade roll 40 will be described later (see FIG. 3).

The transfer roll 50 brings the web 20 continuously fed by the driving rolls 62 and 63 into contact with the lower blade roll 40. The transfer roll 50 rotates at a peripheral velocity ($V_4$) approximately equal to the feeding velocity ($V_3$) of the web 20. In other words, the transfer roll 50 rotates at the peripheral velocity ($V_4$) approximately equal to the peripheral velocity ($V_1$) of the upper blade roll 30 and the lower blade roll 40 described above, or rotates at the peripheral velocity ($V_4$) higher than the peripheral velocity ($V_1$) of the upper blade roll 30 and the lower blade roll 40.

(Configuration of Lower Blade Roll)

Figure 3:
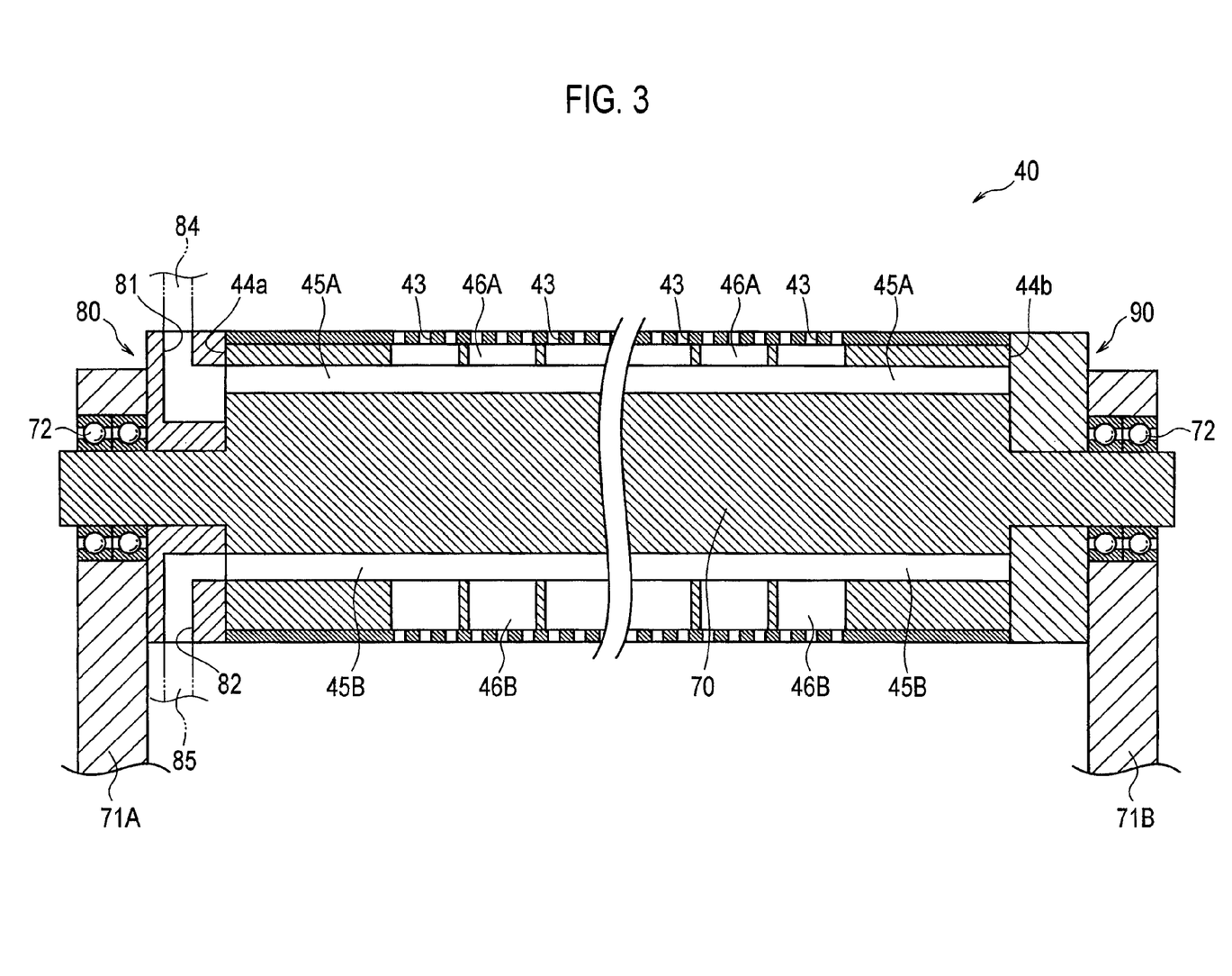
FIG. 3 is a roll width direction sectional view (sectional view along B-B of FIG. 2) showing a lower blade roll 40 according to the first embodiment.

Next, the configuration of the lower blade roll 40 described above will be described with reference to the drawings. FIG. 3 is a roll width direction sectional view (sectional view along B-B of FIG. 2) showing the lower blade roll 40 according to the first embodiment.

As shown in FIG. 3, the lower blade roll 40 is formed integrally with a roll shaft 70. The lower blade roll 40 is configured to be rotated between a pair of frames 71A and 71B by shaft bearings 72.

Formed in the lower blade roll 40 are horizontal holes 45A and 45B penetrating from one end surface 44$a$ to the other end surface 44$b$ of the lower blade roll 40 and opening holes 46A and 46B connecting the horizontal holes 45A and 45B and suction holes 43. The suction holes 43 are formed at positions corresponding to the opening holes 46A and 46B.

A suction member 80 is provided between the lower blade roll 40 and the one frame 71A, whereas a sealing member 90 is provided between the lower blade roll 40 and the other frame 71B.

The suction member 80 and the sealing member 90 each have a diameter approximately equal to the diameter of the lower blade roll 40, and are formed in a disk shape. The suction member 80 and the sealing member 90 are fixed to the frames 71A and 71B, respectively, and are configured so as not to rotate together with the lower blade roll 40.

The suction member 80 is provided with a first suction groove 81 which sucks the continuous film sheet 10A, a second suction groove 82 which sucks the cut film sheet 10 to guide the cut film sheet 10 to the web 20, and a transfer groove 83 for transferring, on the web 20, the cut film sheet 10 sucked onto the outer peripheral surface 41 of the lower blade roll 40.

The first suction groove 81 is formed at a position corresponding to the horizontal hole 45A formed in the lower blade roll 40, and also to a portion of the outer peripheral surface 41 of the lower blade roll 40 around which the continuum of film sheet 10A is wound. The first suction groove 81 is connected with a suction connection pipe 84 connecting the first suction groove 81 and suction air supply means (not shown) which sucks air in the horizontal hole 45A.

The second suction groove 82 is formed at a position corresponding to the horizontal hole 45B formed in the lower blade roll 40, and to a portion of the outer peripheral surface 41 of the lower blade roll 40 around which the cut film sheet 10 is wound. The second suction groove 82 is connected with a suction connection pipe 85 connecting the second suction groove 82 and suction air supply means (not shown) which sucks air in the horizontal hole 45B.

The transfer groove 83 is formed at a position corresponding to the horizontal hole 45B formed in the lower blade roll 40, and to a portion to which the cut film sheet 10 is transferred. The transfer groove 83 is connected with a transfer connection pipe (not shown) connecting the transfer groove 83 and air releasing means (not shown) which releases the suction of air performed by the suction air supply means.

Note that the air releasing means does not necessarily need to release the suction of air performed by the suction air supply means, and may be configured to blow out air through the transfer groove 83 (transfer connection pipe).

In this embodiment, the suction member 80 is provided between the lower blade roll 40 and the one frame 71A. However, it is not limited to this configuration, and the suction member 80 may be additionally provided, instead of the sealing member 90, between the lower blade roll 40 and the other frame 71B. That is, the suction air supply means may perform supply of air from both end sections of the horizontal holes 45A and 45B.

(Alignment of Suction Holes)

Figure 4:
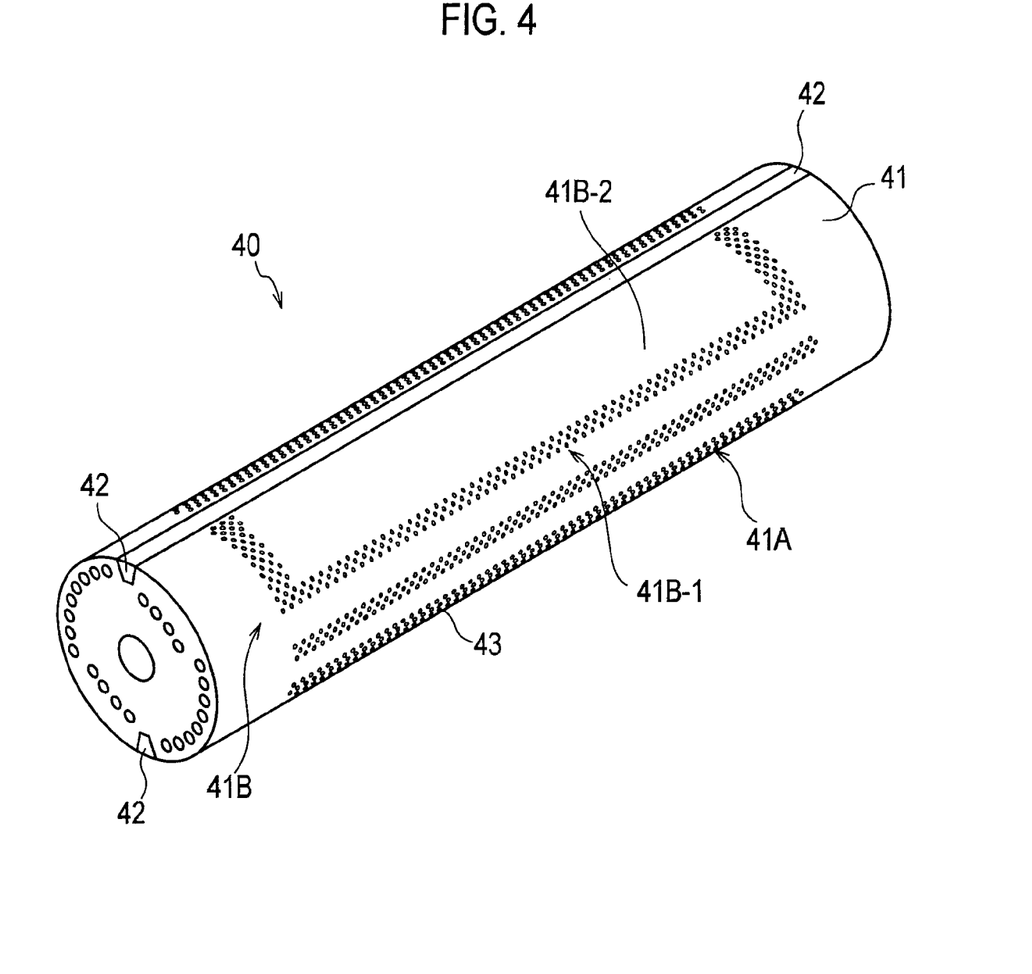
FIG. 4 is a perspective view showing the lower blade roll 40 according to the first embodiment.
Figure 5:
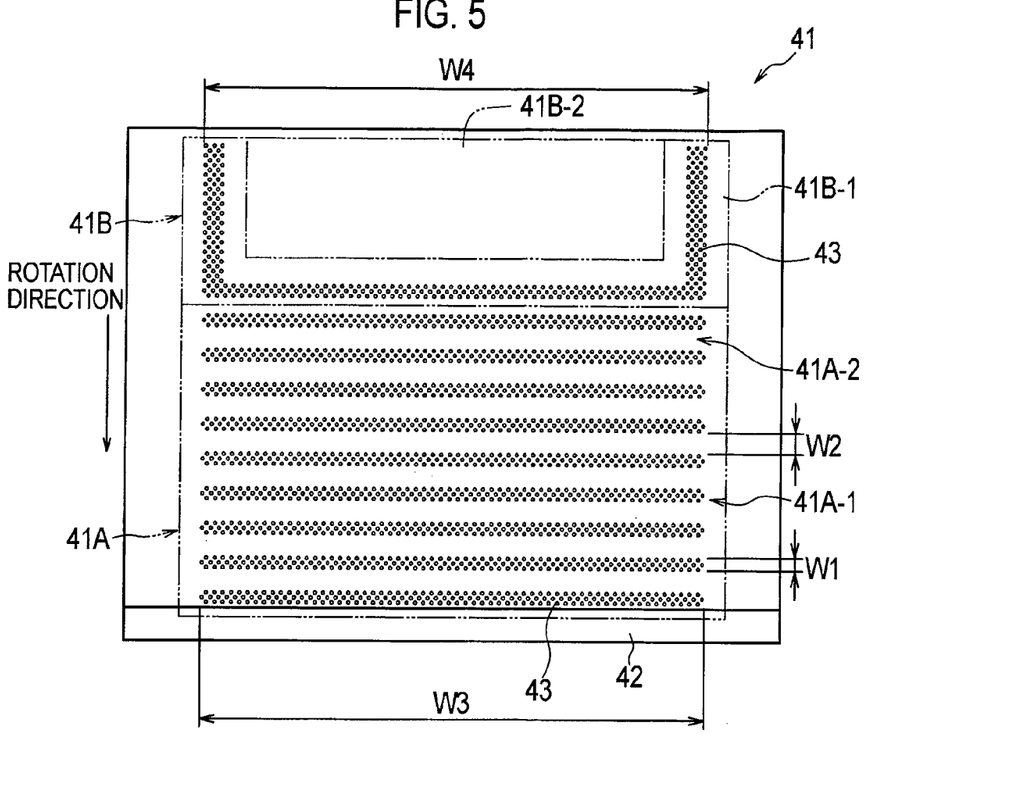
FIG. 5 is a development view showing the lower blade roll 40 according to the first embodiment.
Figure 6:
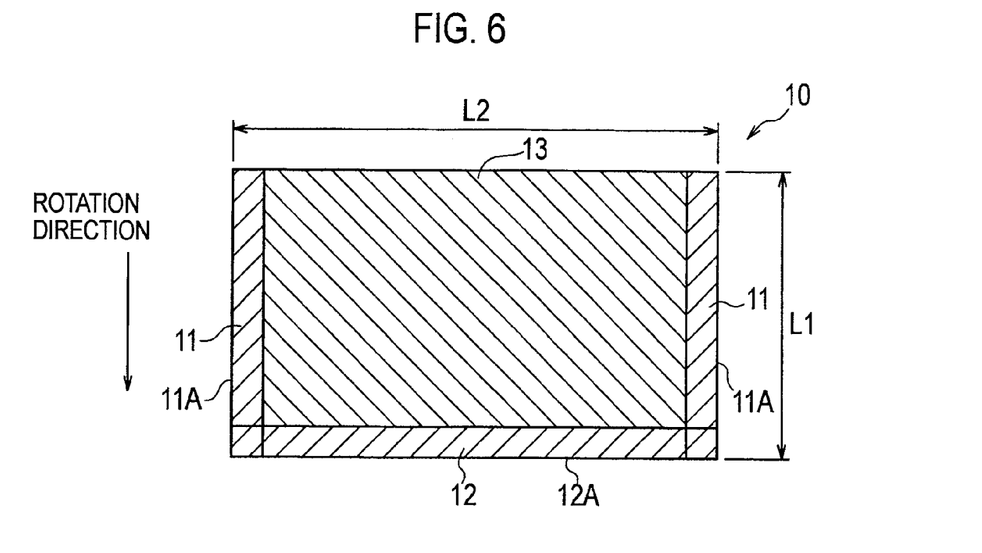
FIG. 6 is an upper view showing a cut film sheet according to the first embodiment.

Next, the alignment of suction holes 43 provided in the lower blade roll 40 described above will be described with reference to the drawings. FIG. 4 is a perspective view showing the lower blade roll 40 according to the first embodiment. FIG. 5 is a development view of the lower blade roll 40 according to the first embodiment. FIG. 6 is an upper view showing the cut film sheet according to the first embodiment.

As shown in FIGS. 4 and 5, the suction holes 43 are formed in a first region 41A and in a second region 41B on the outer peripheral surface 41 of the lower blade roll 40. In the first region 41A and in the second region 41B, the suction holes 43 are arranged at predetermined intervals in the roll peripheral direction and in the roll width direction, and are aligned such that the suction holes 43 that are adjacent in the roll peripheral direction are displaced from each other in the roll width direction (a so-called staggered alignment).

The first region 41A is configured of suction regions 41A-1 each of which having the multiple suction holes 43 formed therein, and non-suction regions 41A-2 each of which having no suction hole 43 formed therein. Accordingly, the suction holding force in the suction regions 41A-1 is stronger than the suction holding force in the non-suction regions 41A-2.

The suction regions 41A-1 and the non-suction regions 41A-2 are provided in the roll width direction. The suction regions 41A-1 and the non-suction regions 41A-2 are provided alternately in the roll peripheral direction.

Each of the regions 41A-1 is configured so that a width (W1) of the suction region 41A-1 in the roll peripheral direction can be shorter than a width (W2) of each non-suction region 41A-2 in the roll peripheral direction.

Each of the regions 41A-1 is configured so that a width (W3) of the suction region 41A-1 in the roll width direction can be wider than the length (L2) of the cut film sheet 10 in the CD direction.

The second region 41B is configured of an edge area 41B-1 having the multiple suction holes 43 formed therein, and a center area 41B-2 having no suction hole 43 formed therein.

Accordingly, the suction holding force in the edge area 41B-1 is stronger than the suction holding force in the center area 41B-2.

The edge area 41B-1 faces both side edge regions 11 and a front end region 12 formed ahead in the proceeding direction of the cut film sheet 10.

As shown in FIG. 6, the both side edge regions 11 of the cut film sheet 10 show regions within 25% of the length (L2) in the CD direction with both end sections 11A of the cut film sheet 10 as the references. The front end region 12 of the cut film sheet 10 formed ahead in the proceeding direction shows a region within 50% of the length (L1) in the MD direction with a front end section 12A of the cut film sheet as the reference. Note that the area of the center area 41B-2 needs to have an area that is 50% or more of a whole area of the cut film sheet 10.

A maximum width (W4) of the edge area 41B-1 in the roll width direction is approximately equivalent to the width (W3) of the suction region 41A-1 in the roll width direction described above, i.e., configured to be wider than the length (L2) of the cut film sheet 10 in the CD direction.

The center area 41B-2 faces a remaining region 13 which is a region other than the both side edge regions 11 and the front end region 12 formed ahead in the proceeding direction of the cut film sheet 10. Note that, as shown in FIG. 6, the remaining region 13 shows a region inside the both side edge regions 11 and the front end region 12 formed ahead in the proceeding direction of the cut film sheet 10 described above.

(Operation of Intermittent Cutting Transferring Device)

Next, the operation of the intermittent cutting transferring device 1 according to the first embodiment will be described briefly.

In a first step, the intermittent cutting transferring device 1 guides the continuum of film sheet 10A between the blade 32 and the anvil element 42 with the continuum of film sheet 10A being sucked onto the outer peripheral surface 41 of the lower blade roll 40 by the suction of the suction air supply means through the suction holes 43 formed in the first region 41A (suction region 41A-1) on the outer peripheral surface 41 of the lower blade roll 40.

At this time, the continuum of film sheet 10A slides on the outer peripheral surface 41 of the lower blade roll 40 to be guided between the blade 32 and the anvil element 42 because the upper blade roll 30 and the lower blade roll 40 rotate at the peripheral velocity (V1) higher than the velocity (V2) in which the continuum of film sheet 10A is fed to the lower blade roll 40.

In a second step, the intermittent cutting transferring device 1 intermittently cuts the continuum of film sheet 10A by bringing the blade 32 and the anvil element 42 into contact with each other. The cut film sheet 10 is thus formed. Note that the length (L1) of the cut film sheet 10 in the MD direction is shorter than the length (L2) of the cut film sheet 10 in the CD direction.

In a third step, the intermittent cutting transferring device 1 guides the cut film sheet 10 to the web 20 while the cut film sheet 10 is being sucked onto the outer peripheral surface 41 of the lower blade roll 40 by the suction of the suction air supply means, through the suction holes 43 formed in the second region 41B (edge area 41B-1) on the outer peripheral surface 41 of the lower blade roll 40.

That is, the cut film sheet 10 is sucked onto the outer peripheral surface 41 of the lower blade roll 40 with the both side edge regions 11 and the front end region 12 formed ahead in the moving direction facing the edge area 41B-1 of the second region 41B as well as the remaining region 13 facing the center area 41B-2 of the second region 41B.

In a fourth step, the intermittent cutting transferring device 1 transfers the cut film sheet 10 sucked onto the outer side surface 41 of the lower blade roll 40 to the web 20 by releasing the suction of air performed by the suction air supply means.
(Operation and Effect of First Embodiment)

In the intermittent cutting transferring device 1 according to the first embodiment, the suction holding force of the edge area 41B-1 is stronger than the suction holding force in the center area 41B-2. On this assumption, the operation and effect achieved until the cut film sheet 10 is guided to the web 20 (at the time of film feeding) will first be described.

In the remaining region 13 other than the both side edge regions 11 and the front end region 12, the cut film sheet 10 comes into the suction holes 43 in less cases compared to the both side edge regions 11 and the front end region 12, whereby the formation of a wrinkle of the cut film sheet 10 can be suppressed. Moreover, the cut film sheet 10 is pulled toward the edge area 41B-1 sides. Accordingly, even when the wrinkle is formed in the cut film sheet 10, the wrinkle formed in the cut film sheet 10 can be smoothed out in the remaining region 13 other than the both side edge regions 11 and the front end region 12.

Next, the operation and effect achieved when the cut film sheet 10 is transferred to the web 20 (at the time of film transfer) will be described.

When the cut film sheet 10 makes contact on the web 20 firstly with the front end region 12. At this time, the air releasing means releases the suction of air performed by the suction air supply means, whereby the cut film sheet 10 makes contact on the web 20 firstly with the center area 41B-2 having a weak suction holding force. That is, since the suction holding force in the center area 41B-2 is weaker than the suction holding force in the edge area 41B-1, it becomes easier to transfer the cut film sheet 10 to the web 20 from the center area 41B-2 having a weak suction holding force, as compared to the case where the suction holding force is the same in the entire region of the outer peripheral surface 41 of the lower blade roll 40. Thus, the formation of a wrinkle in the cut film sheet 10 can be suppressed.

The intermittent cutting transferring device 1 according to the first embodiment has no suction hole 43 formed in the center area 41B-2. Accordingly, at the time of the film feeding and the film transfer, the cut film sheet 10 is not sucked onto the outer peripheral surface 41 of the lower blade roll 40 in the center area 41B-2, whereby the cut film sheet 10 does not come into the suction hole 43. Thus, the formation of a wrinkle in the cut film sheet 10 can be suppressed.

Note that, when the length (L1) of the cut film sheet 10 in the MD direction is shorter than the length (L2) in the CD direction, the weight of the cut film sheet easily becomes uneven, and a wrinkle is easily formed in the cut film sheet 10 by a contact failure of the blade and the anvil element or a wear of the blade.

On the other hand, in the intermittent cutting transferring device 1 according to the first embodiment, as described above, the suction holding force in the edge area 41B-1 is stronger than the suction holding force in the center area 41B-2. Accordingly, the formation of a wrinkle in the cut film sheet 10 can be suppressed. Even when the wrinkle is formed in the cut film sheet 10, a wrinkle formed in the cut film sheet 10 can be smoothed out. Thus, it is particularly effective when the length (L1) of the cut film sheet 10 in the MD direction is shorter than the length (L2) in the CD direction.

The intermittent cutting transferring device 1 according to the first embodiment is configured so that the maximum width (W4) of the edge area 41B-1 in the roll width direction is approximately equal to the width (W3) of the suction region 41A-1 in the roll width direction described above, or, in other words, so that the maximum width (W4) is wider than the length (L2) of the cut film sheet 10 in the CD direction. Accordingly, the both side edge regions 11 and the front end region 12 formed ahead in the proceeding direction of the cut film sheet 10 can reliably be sucked by the suction through the suction holes 43 formed in the edge area 41B-1. Thus, at the time of transfer, the both side edge regions 11 and the front end region 12 formed ahead in the proceeding direction of the cut film sheet 10 can be prevented from being bent.

[Second Embodiment]

Hereinafter, the configuration of the intermittent cutting transferring device 1 according to a second embodiment will be described with reference to the drawings. Note that the same portions as those of the above-described intermittent cutting transferring device 1 according to the first embodiment are denoted by the same reference numerals, and differing portions will mainly be described.

Specifically, the first embodiment described above has no suction hole 43 formed in the center area 41B-2. In contrast, in the second embodiment, the suction holes 43 are formed in the center area 41B-2.
(Configuration of Lower Blade Roll)

Figure 7:
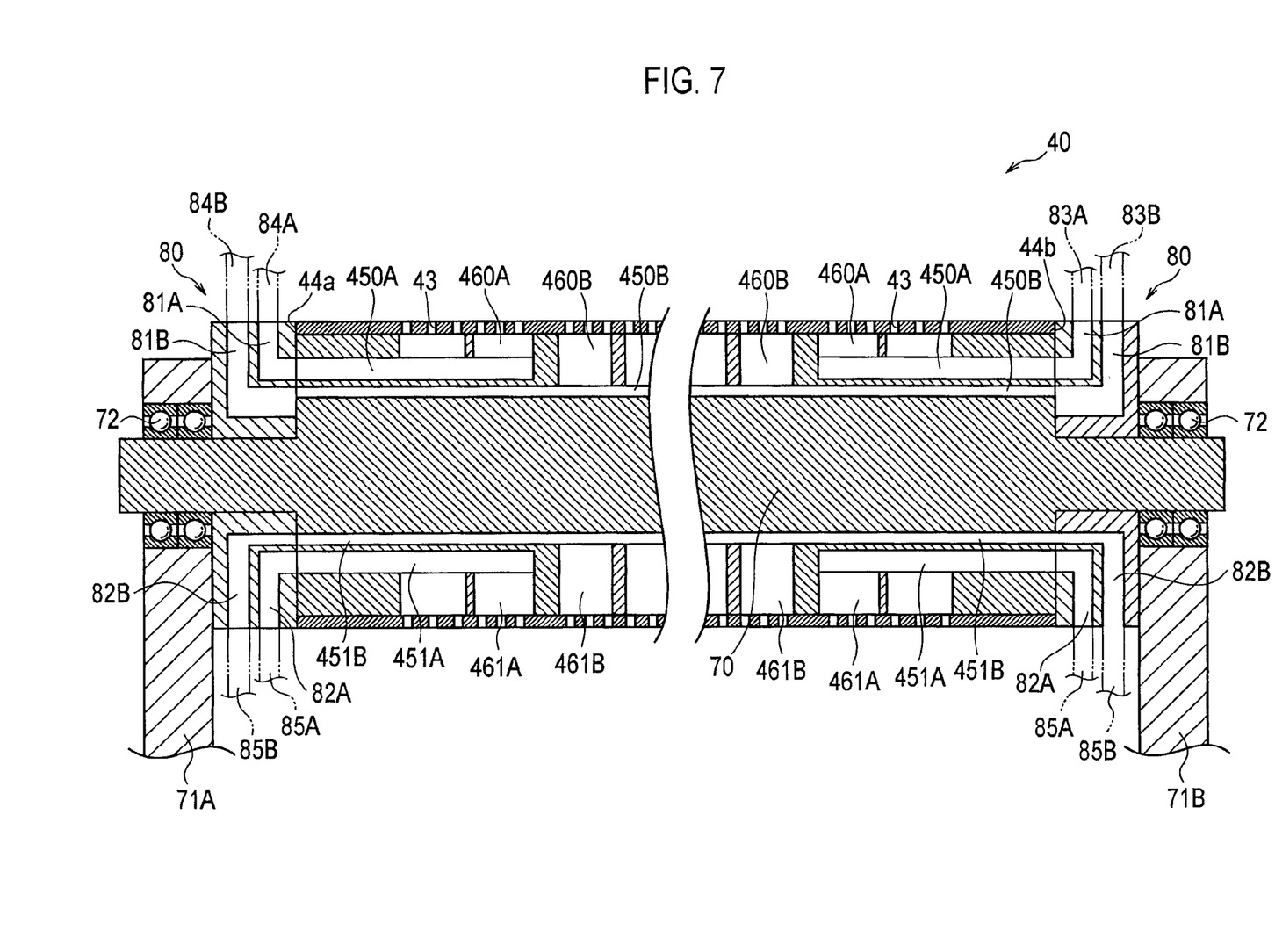
FIG. 7 is a roll width direction sectional view showing the lower blade roll 40 according to a second embodiment.

First, the configuration of the lower blade roll 40 according to the second embodiment will be described with reference to the drawing. FIG. 7 is a roll width direction sectional view showing the lower blade roll 40 according to the second embodiment.

As shown in FIG. 7, the intermittent cutting transferring device 1 is configured so that at least one of the suction holding force in the edge area 41B-1 and the suction holding force in the center area 41B-2 would be variable.

In addition to that between the lower blade roll 40 and the one frame 71A, the suction member 80 is provided also between the lower blade roll 40 and the other frame 71B.

A first horizontal hole 450A and a first opening hole 460A are formed in the lower blade roll 40. The first horizontal hole 450A penetrates from the one end surface 44a to the other end surface 44b of the lower blade roll 40, and the first opening hole 460A connects the first horizontal hole 450A and the suction holes 43 formed in the edge area 41B-1.

In addition, a second horizontal hole 450B and a second opening hole 460B are also formed in the lower blade roll 40. The second horizontal hole 450B extends approximately in parallel to the first horizontal hole 450A and penetrates from the one end surface 44a to the other end surface 44b of the lower blade roll 40, and the second opening hole 460B connects the second horizontal hole 450B and the suction holes 43 formed in the center area 41B-2.

The first horizontal hole 450A is connected to suction air supply means (not shown) through a first suction groove 81A and a suction connection pipe 84A. The second horizontal hole 450B is connected to suction air supply means (not shown), which is provided separately from the suction air supply means connected with the first horizontal hole 450A, through a first suction groove 81B and a suction connection pipe 84B.

Further, a third horizontal hole 451A and a third opening hole 461A are provided in the lower blade roll 40. The third horizontal hole 451A penetrates from the one end surface 44a to the other end surface 44b of the lower blade roll 40, and the third opening hole 461A connects the third horizontal hole 451A and the suction holes 43 formed in the edge area 41B-1.

In addition, a fourth horizontal hole 451B and a fourth opening hole 461B are also formed in the lower blade roll 40. The fourth horizontal hole 451B extends approximately in parallel to the third horizontal hole 451A and penetrates from the one end surface 44a to the other end surface 44b of the lower blade roll 40, and the fourth opening hole 461B connects the fourth horizontal hole 451B and the suction holes 43 formed in the center area 41B-2.

The third horizontal hole 451A is connected to suction air supply means (not shown) through a second suction groove 82A and a suction connection pipe 85A. The fourth horizontal hole 451B is connected to suction air supply means (not shown), which is provided separately from the suction air supply means connected with the third horizontal hole 451A, through a second suction groove 82B and a suction connection pipe 85B.

(Alignment of Suction Holes)

Figure 8:
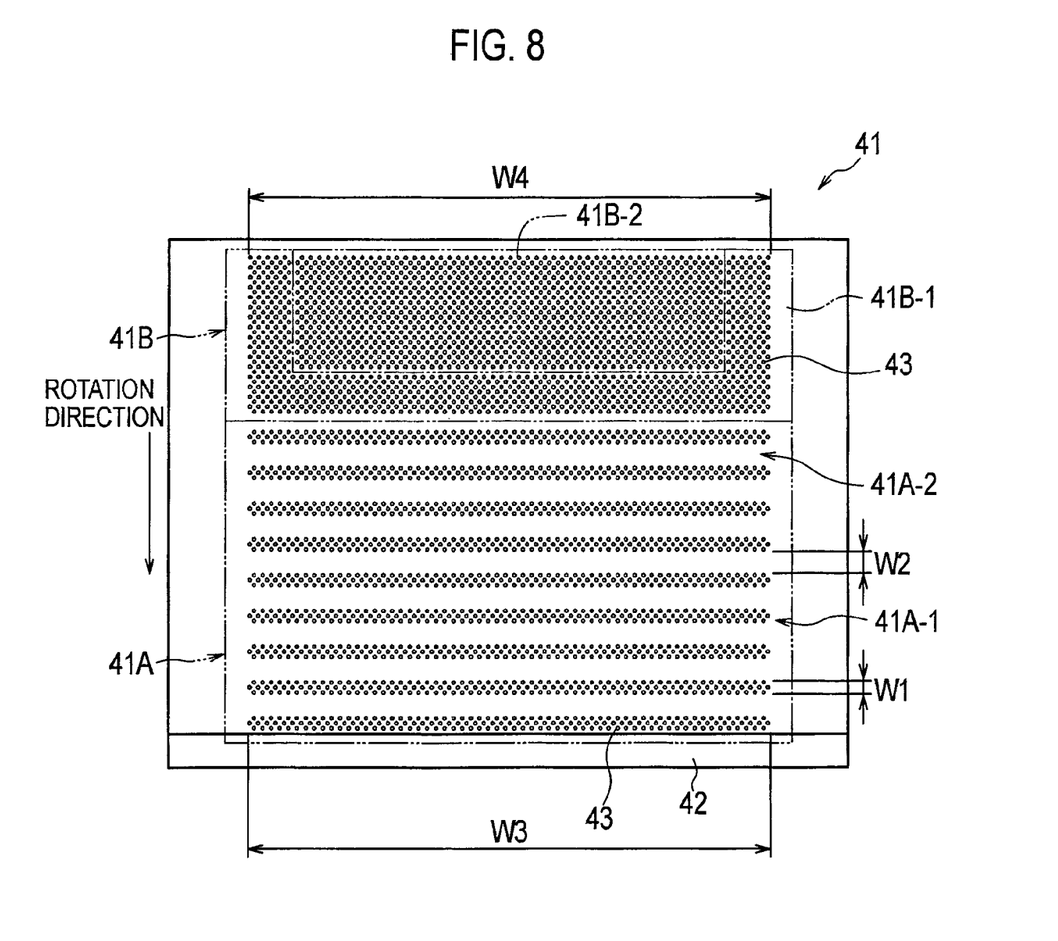
FIG. 8 is a development view showing the lower blade roll 40 according to the second embodiment.

Next, the alignment of the suction holes 43 according to the second embodiment will be described with reference to the drawing. FIG. 8 is a development view showing the lower blade roll 40 according to the second embodiment.

As shown in FIG. 8, the suction holes 43 are formed in the entire region of the second region 41B. Note that the suction holding force in the edge area 41B-1 is stronger than the suction holding force in the center area 41B-2.

That is, since the suction force of the suction air supply means through the suction holes 43 formed in the edge area 41B-1 is stronger than the suction force of the suction air supply means through the suction holes 43 formed in the center area 41B-2, the suction holding force in the edge area 41B-1 can be made stronger than the suction holding force in the center area 41B-2.

In the description of the above second embodiment, the suction force of the suction air supply means through the suction holes 43 in the edge area 41B-1 is stronger than the suction force of the suction air supply means through the suction holes 43 formed in the center area 41B-2. Note, however, that it is not limited thereto, and the aperture ratio of the suction holes 43 formed in the edge area 41B-1 may be larger than the aperture ratio of the suction holes 43 formed in the center area 41B-2.

(Operation and Effect of Second Embodiment)

In addition to the operation and effect of the first embodiment described above, in the intermittent cutting transferring device 1 according to the second embodiment, the edge area 41B-1 and the center area 41B-2 can be set in accordance with the size of the cut film sheet 10 (for example, the length (L2) of the cut film sheet 10 in the CD direction). Accordingly, the intermittent cutting transferring device 1 according to the second embodiment is able to manufacture the cut film sheet 10 in various sizes.

[Other Embodiments]

As described above, the content of the present invention has been disclosed through the embodiments of the present invention, but the descriptions and drawings forming a part of the disclosure should not be construed to limit the present invention.

In the embodiments, two blades 32 are provided on the outer peripheral surface 31 of the upper blade roll 30. However, it is not limited thereto, and at least one blade 32 may be provided. In the same manner, at least one anvil element 42 may be provided on the outer peripheral surface 41 of the lower blade roll 40.

In the embodiments, the first region 41A is configured of the suction region 41A-1 and the non-suction region 41A-2, but it is not limited thereto. It is needless to say that the suction holes 43 may be formed in the entire region.

Various alternative embodiments, examples, and application technology will become clear to those skilled in the art from this disclosure. Thus, the technical scope of the present invention is defined only by the claims appropriate from the descriptions above.

What is claimed is:

1. An intermittent cutting transferring device configured to cut a first web into individual sheets and to intermittently transfer the individual sheets onto a second web being continuously fed, said device comprising:
    an upper blade roll including at least one blade on an outer peripheral surface thereof; and
    a lower blade roll including, on an outer peripheral surface thereof, at least one anvil element and a plurality of suction holes,
    wherein
    the upper blade roll and the lower blade roll are rotatable in opposite moving directions at approximately the same peripheral velocity, which is higher than a velocity in which the first web is fed to the lower blade roll, and equal to or lower than a feeding velocity of the second web,
    the blade and the anvil element are configured to guide the first web therebetween while the first web is being sucked onto the outer peripheral surface of the lower blade roll by a suction through the suction holes formed in a first region on the outer peripheral surface of the lower blade roll,
    the blade and the anvil element are adapted to be brought into contact with each other to intermittently cut the first web into the individual sheets,
    each of the individual sheets cut from the first web is arranged to be guided and transferred onto the second web while the sheet is being sucked onto the outer peripheral surface of the lower blade roll by a suction through the suction holes formed in a second region on the outer peripheral surface of the lower blade roll,
    the cut sheet is arranged to be sucked onto the outer peripheral surface of the lower blade roll at a position where both side edge regions of the cut sheet and a front end region of the cut sheet face an edge area of the second region while a remaining region of the cut sheet faces a center area of the second region,
    a suction holding force in the edge area corresponding to said front end region and said side edge regions of the cut sheet is stronger than a suction holding force in the center area corresponding to said remaining region of the cut sheet,
    the second region has
        the center area free of the suction holes; and
        a suction region along the edge area and provided with suction holes and partially surrounding the center area;
    a maximum width of the suction region in a roll width direction is substantially equivalent to a width of the first region in the roll width direction,
    the suction region in the second region comprises two lateral regions opposite each other in the roll width direction and a transverse region extending in the roll width direction to connect the lateral regions, and
    the suction holes are evenly distributed throughout the lateral regions and the transverse region.

2. The intermittent cutting transferring device according to claim 1, wherein the suction holes are provided in the edge area and are not provided in the center area therefore the suction holding force in the edge area is stronger than the suction holding force in the center area.

3. The intermittent cutting transferring device according to claim 1, wherein at least one of the suction holding force in the edge area and the suction holding force in the center area is variable.

4. The intermittent cutting transferring device according to claim 1, wherein a length of the second region in the moving direction is shorter than a width of the second region in the roll width direction crossing the moving direction, so as to suck the cut sheet having a length in the moving direction shorter than a length in the roll width direction.

5. The intermittent cutting transferring device according to claim 1, wherein the suction holes in the edge area are arranged along
- opposite sides of the second region in the moving direction and
- a front end of the second region in the roll width direction crossing the moving direction.

6. The intermittent cutting transferring device according to claim 1, wherein the suction holes in the first region are arranged in rows along the roll width direction crossing the moving direction.

7. The intermittent cutting transferring device according to claim 1, wherein the width of the first region is configured to be wider than a length of the cut sheet in the roll width direction.

8. The intermittent cutting transferring device according to claim 1, wherein the first region is entirely located downstream of the second region in the moving direction of the lower blade roll.

9. The intermittent cutting transferring device according to claim 6, wherein
- the rows of the suction holes in the first region are grouped into several groups spaced from one another in the moving direction,
- a distance between adjacent two rows in the moving direction in each group is smaller than a distance between adjacent two groups in the moving direction, and
- the suction holes in the rows in each group are staggered relative to each other in both the moving direction and the roll width direction.

10. The intermittent cutting transferring device according to claim 9, wherein the rows of the suction holes in the first region have substantially same widths in the roll width direction.

11. The intermittent cutting transferring device according to claim 9, wherein a dimension of each of the groups in the moving direction is shorter than the distance between two adjacent rows in the moving direction.

\* \* \* \* \*